United States Patent [19]

Puno et al.

[11] Patent Number: 5,496,321
[45] Date of Patent: Mar. 5, 1996

[54] ROD ANCHOR SEAT HAVING A SLIDING INTERLOCKING ROD CONNECTOR

[75] Inventors: Rolando M. Puno, Prospect, Ky.; Philip Mellinger, Worthington, Ohio; J. Abbott Byrd, III, Virginia Beach, Va.

[73] Assignee: Cross Medical Products, Inc., Columbus, Ohio

[21] Appl. No.: 355,100

[22] Filed: Dec. 12, 1994

Related U.S. Application Data

[63] Continuation of Ser. No. 155,430, Nov. 19, 1993, abandoned.

[51] Int. Cl.$^6$ ............................................. A61B 17/70
[52] U.S. Cl. ................................................. 600/61
[58] Field of Search ............................ 606/59, 60, 61, 606/72, 73; 403/235, 331, 333, 381

[56] References Cited

U.S. PATENT DOCUMENTS

| | | |
|---|---|---|
| 483,342 | 9/1892 | Bolte . |
| 900,717 | 10/1908 | Feaster . |
| 3,019,504 | 2/1962 | Castagliuolo . |
| 3,752,203 | 8/1973 | Hill, Jr. . |
| 4,011,602 | 3/1977 | Rybicki et al. . |
| 4,019,298 | 4/1977 | Johnson, IV .............................. 403/331 |
| 4,289,124 | 9/1981 | Zickel . |
| 4,347,845 | 9/1982 | Mayfield ................................... 606/61 |
| 4,411,259 | 10/1983 | Drummond . |
| 4,611,581 | 9/1986 | Steffee . |
| 4,641,636 | 2/1987 | Cotrel . |
| 4,648,388 | 3/1987 | Steffee . |
| 4,653,481 | 3/1987 | Howland et al. . |
| 4,655,199 | 4/1987 | Steffee . |
| 4,658,809 | 4/1987 | Ulrich et al. . |
| 4,719,905 | 1/1988 | Steffee . |
| 4,771,767 | 9/1988 | Steffee . |
| 4,805,602 | 2/1989 | Puno et al. . |
| 4,815,453 | 3/1989 | Cotrel . |
| 4,887,595 | 12/1989 | Heinig et al. . |
| 4,887,596 | 12/1989 | Sherman ................................... 606/72 |
| 4,913,134 | 4/1990 | Luque . |
| 4,950,269 | 8/1990 | Gaines, Jr. ................................ 606/61 |
| 5,005,562 | 4/1991 | Cotrel . |
| 5,024,213 | 6/1991 | Asher et al. . |
| 5,067,955 | 11/1991 | Cotrel . |
| 5,084,049 | 1/1992 | Asher et al. . |
| 5,113,685 | 5/1992 | Asher et al. . |
| 5,120,171 | 6/1992 | Lasner . |
| 5,129,900 | 7/1992 | Asher et al. . |
| 5,190,543 | 3/1993 | Schläpfer . |
| 5,207,678 | 5/1993 | Harms et al. . |
| 5,257,993 | 11/1993 | Asher et al. ............................... 606/61 |
| 5,261,913 | 11/1993 | Marnay ..................................... 606/61 |

FOREIGN PATENT DOCUMENTS

| | | |
|---|---|---|
| 4107480 | 9/1992 | Germany ................................... 606/61 |
| 167228 | 7/1921 | United Kingdom . |
| 2173104 | 10/1986 | United Kingdom . |
| 87/07134 | 12/1987 | WIPO . |

*Primary Examiner*—Tamara L. Graysay
*Attorney, Agent, or Firm*—Hudak & Shunk Co.

[57] ABSTRACT

A spinal implant assembly is provided having a top loading anchor which is fixed to a spinal member by means of a hook or screw. The anchor includes a seat having a channel to receive a stabilizer rod and a sliding interconnecting closure member which slides in a longitudinal direction relative to the anchor seat to form an integral closed anchor seat assembly. The closure member includes retaining flanges which dove tail relative to undercut retaining flanges of the seat member so as to prohibit the sliding closure member from being dislodged from the closure from the seat channel, as well as inhibit the splaying of the seat member in response to forces which may be imposed upon the seat member during derotation of the spine. In addition, the seat member includes a boss and/or hollow to form a biased lock and compression screw to lock the rod in position relative to the anchor. An instrument is provided which holds the slide for assembly in a spring loaded ball plunger.

13 Claims, 6 Drawing Sheets

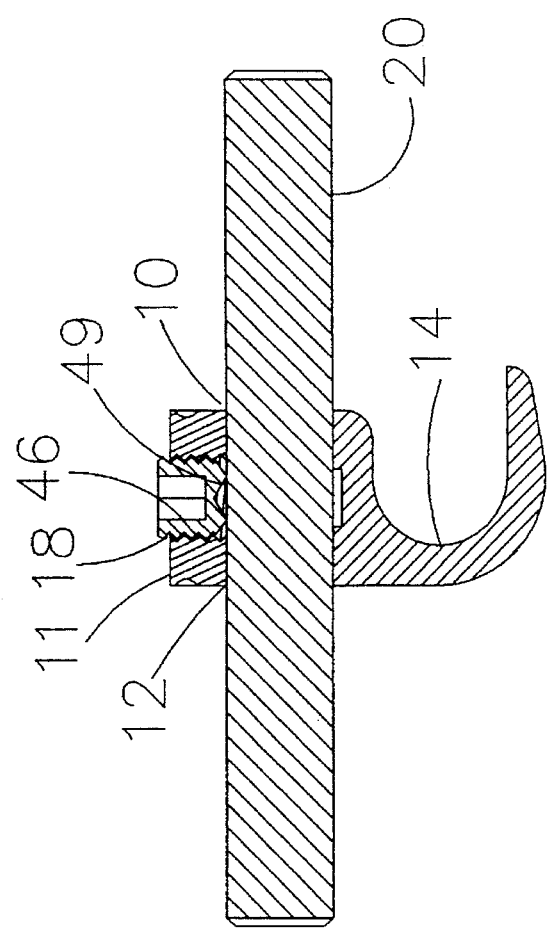
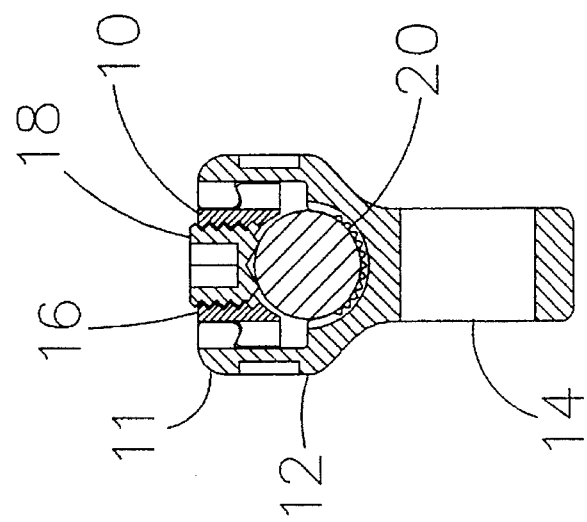
FIG. 3
FIG. 4

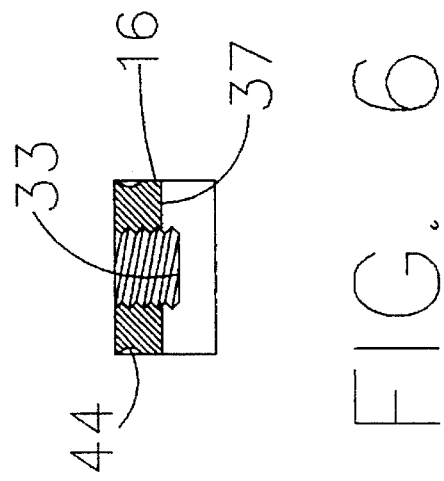
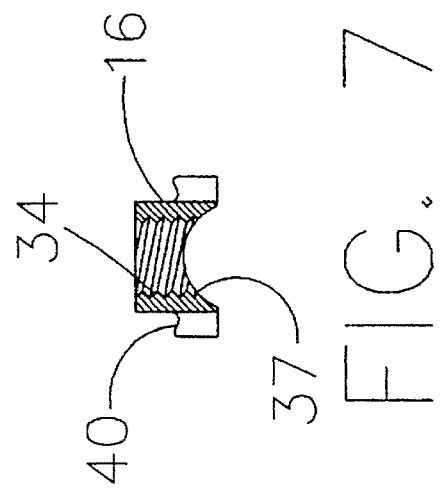
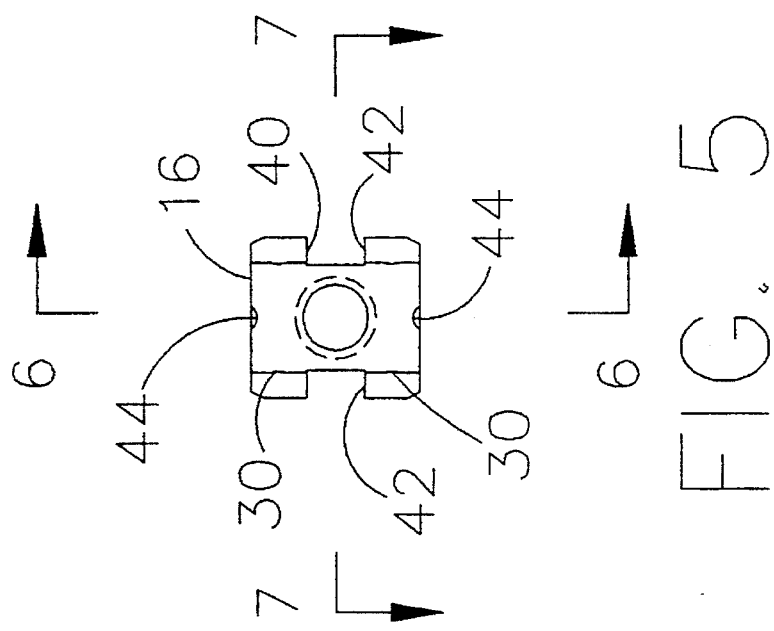

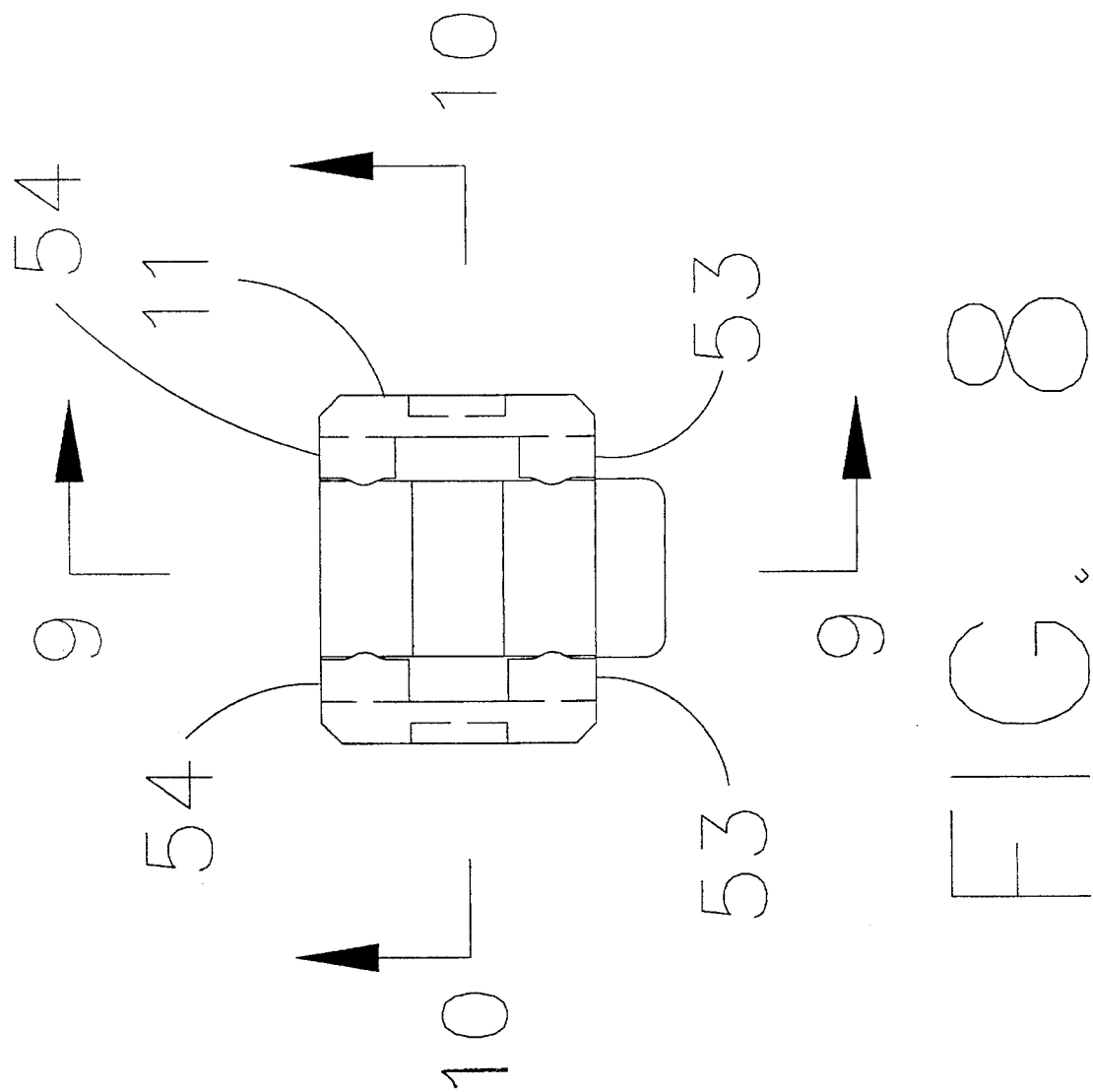

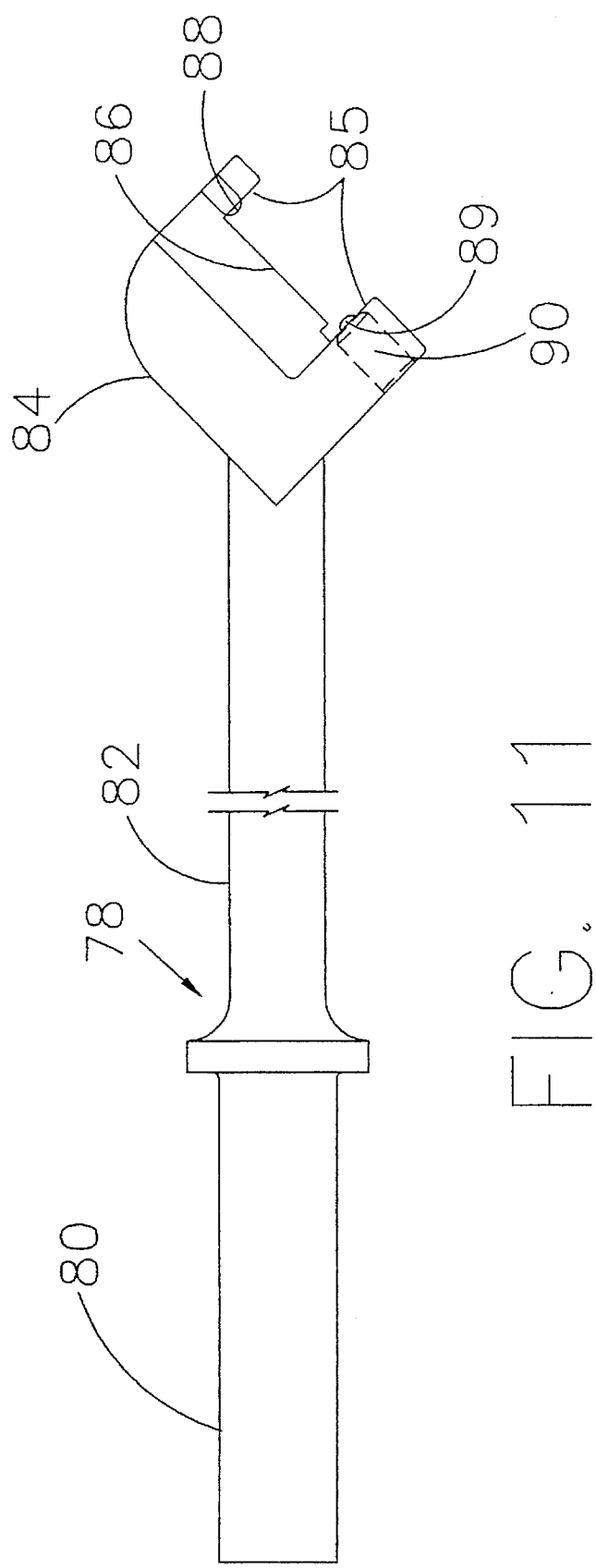

ROD ANCHOR SEAT HAVING A SLIDING INTERLOCKING ROD CONNECTOR

This application is a continuation of application Ser. No. 08/155,430, filed on Nov. 19, 1993, by Rolando M. Puno, Philip Mellinger and J. Abbott Byrd III, for "A Rod Anchor Seat Having A Sliding Interlocking Rod Connector", now abandoned.

FIELD OF THE INVENTION

This invention relates to orthopedic implants, and more particularly to a bone interface anchor for holding a stabilization rod. The anchor can be adjusted after implantation to receive a stabilizer, and is locked into position after assembly.

BACKGROUND

As surgical techniques have advanced, it has become increasingly common for surgeons to use specially designed hardware for the internal fixation of bones. A particular area of concentration for the recent development of this technology has been the spine. Internal fixation is used most frequently in the spine in conjunction with vertebral fusion, and also for the manipulation of the spine to correct spinal deformities such as scoliosis.

There are several important criteria for a hardware system which is used for internal fixation:

1. The implant should provide rigidity as is indicated, generally along the long axis of the patient's spine.
2. The system should be able to accommodate a broad variation in the size and shape of the spinal member with which it is used. For example, t:he surgeon may wish to use the implant on a variety of individuals. In addition, the difference in the area and size of the point of fixation is compounded by the change in the shape of the vertebrae over the length of the full spinal column. Since it is an advantage to allow the surgeon to master implanting a particular type of assembly, it is preferable if the same or similar anchoring means can be used for a variety of locations. This advantage results in cost efficiency of inventory as well as efficiencies with respect to minimizing the operating time.
3. The hardware must be able to apply and oppose considerable stresses and strains. Thus, the anchor means must be securely fixed to the bone, and the stabilizer must be securely fixed with regard to the anchor means. Moreover, it is desirable to have the integrity to resist breaking.
4. The system should be designed for ease of implantation and removal. Implant hardware is relatively small and therefore somewhat difficult to manipulate. Any difficulty with assembly is compounded by the fact that the assembly occurs during surgery and in a living being. Therefore, it is critical that the hardware is designed with the surgeon's convenience in mind, i.e., to limit the time required and the stress required to implant an assembly. Consequently, a fixation system should be designed to the extent possible for easy assembly while maintaining the option of removal where necessary.

SUMMARY OF THE INVENTION

The present invention relates to a top-loading rod anchor which has an interlocking sliding member to close the anchor about the rod. The anchor assembly in the present invention includes an anchor having a center slot to allow insertion of the sliding member from the center. The slot includes a lateral undercut which mates with the flanges on the sliding member.

Accordingly, it is an object of the present invention to provide a vertebral anchor means which is top-loading, but which converts to a two-piece closed anchor for derotation of the spine. Closed anchor refers to an anchor which is at least substantially partially closed about the rod so that the anchor means will withstand hoop stresses introduced by manipulating the rod within the anchor. It is a further object of the invention to provide a sliding interconnecting member which cooperates an said anchor seat means by an axially sliding and which has a positive stop which removably locks said sliding member into cooperation with said anchor means.

BRIEF DESCRIPTION OF DRAWINGS

FIG. 3 is a cross-section of the assembled components of FIG. 1 taken along line 3—3 of FIG. 2;

FIG. 4 is a cross-section of the assembled components taken along line 4—4 of FIG. 1;

FIG. 5 is a top view of the sliding interlocking seat closure member as shown in FIG. 1;

FIG. 6 is a cross-section of the closure member taken along line 6—6 of FIG. 5;

FIG. 7 is a cross-section of the sliding member taken along line 7—7 of FIG. 5; and FIG. 8 is a top plan view of the anchor used with the implant assembly of FIG. 1;

FIG. 11 is an instrument for the alignment and implantation of the sliding interconnecting rod closure member as shown in FIGS. 1-4.

DETAILED DESCRIPTION OF THE INVENTION

Figure 2:
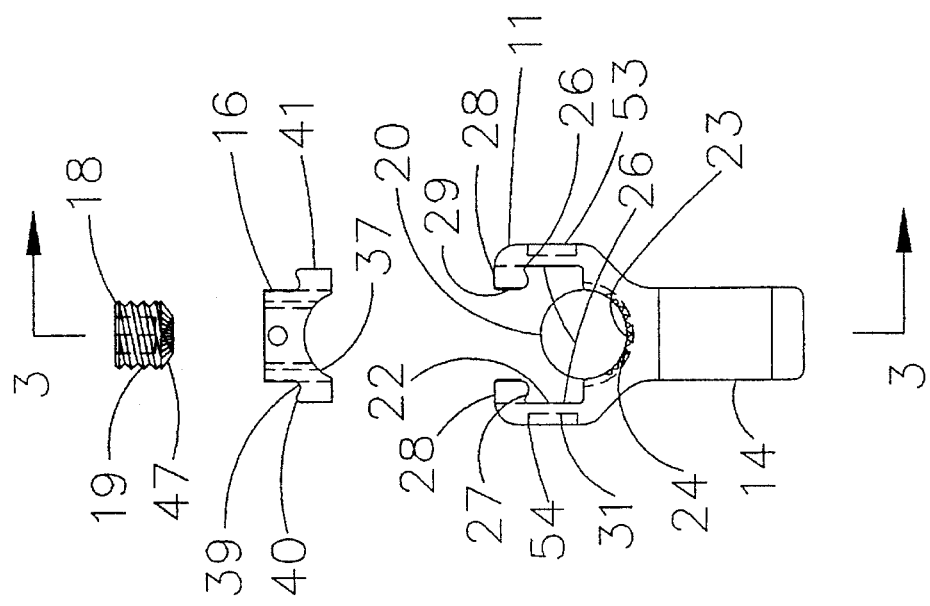
FIG. 2 is an exploded front view of the implant assembly in accordance with the present invention.
Figure 1:
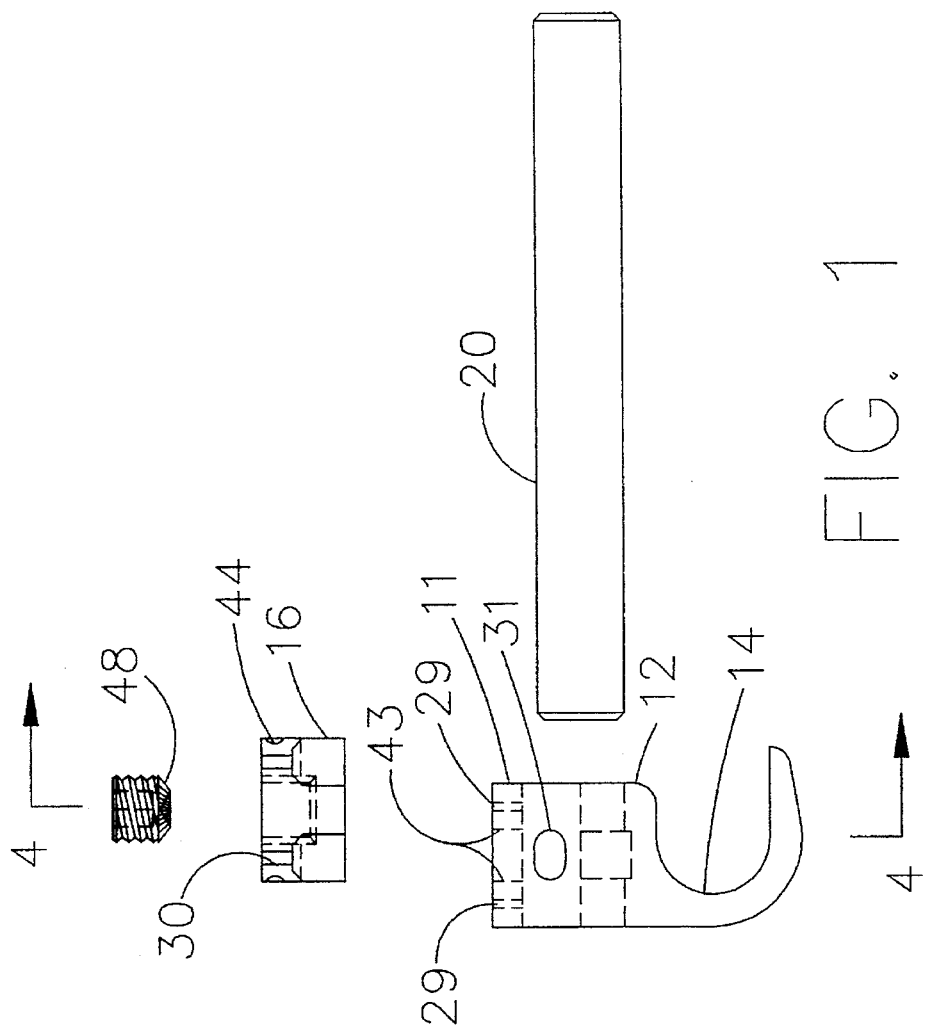
FIG. 1 is an exploded side view of the implant assembly in accordance with the present invention.
Figure 10:
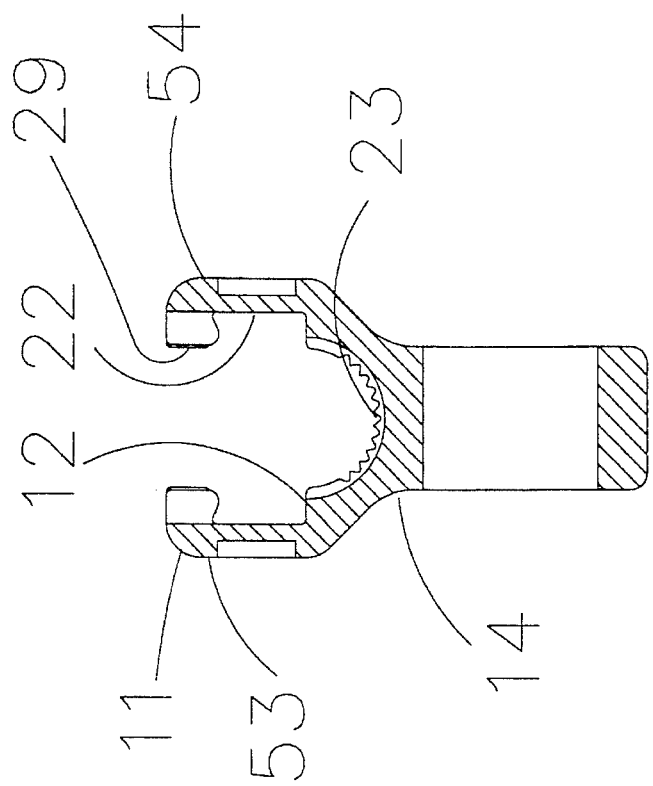
FIG. 10 is a front cross-sectional view taken along line 10—10 of the anchor of FIG. 8.
Figure 9:
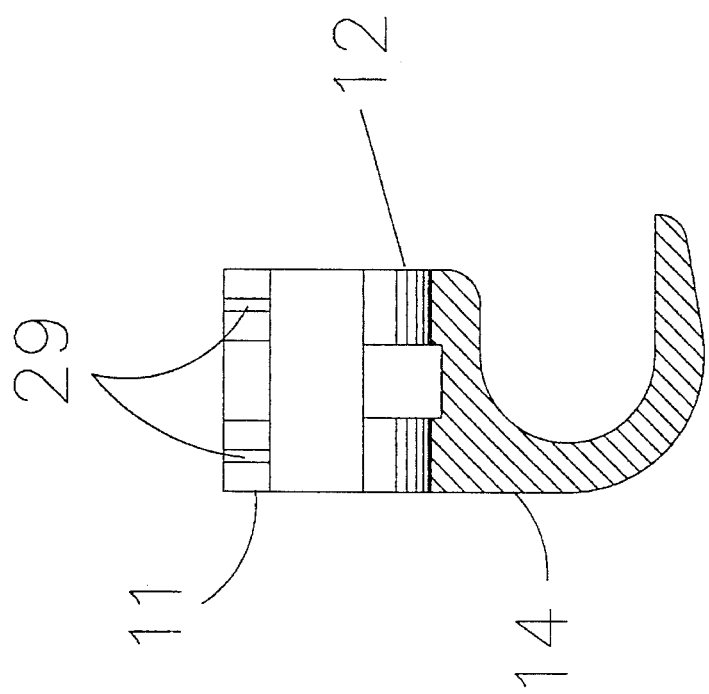
FIG. 9 is a side cross-sectional view taken along line 9—9 of the anchor of FIG. 8.

FIG. 1 illustrates an exploded side view of the spinal implant assembly of the present invention. The implant assembly 10 comprises a stabilization means, i.e., rod 20, and an implant anchor 11. The anchor includes a seat 12 which is fixed to the spine by fixation means, in this case, a hook 14. However, the invention could also be practiced with other fixation means such as a bone screw. The seat 12 includes a recess 23 which receives the rod about its longitudinal axis and which is loaded from the top of the seat. The seat is closed by a sliding interconnecting closure member 16 which has a sliding interlocking engagement with seat member 12. More specifically, the closure member 16 is dropped into an engagement on the rod 20 and slid in a direction along the rods' longitudinal axis so as to form an interlocking engagement with the seat 12. A set screw 18 cooperates with the closure member to apply a compressive force on the rod and secure the rod relative to the seat member.

The seat 12 includes a channel 22 which has in its bottom a rod recess 23 which is contoured to accept the rod 20. Optionally, the rod recess 23 may include a surface interface so as to increase the compressive interface between the rod 20 and the seat, such as interrupted serrations.

The channel 22 includes in its upper portion a recess 26 which is formed on the inside of a seat shoulder 27. This forms an interference fit which removably locks the closure member 16 and the seat 12 when the closure member 16 is slid along the longitudinal axis of the rod into a closed position. In addition, the flange members 28 which form the seat shoulder 27 include a slight protuberance 29 which mates with grooves 30 on the closure member 16 to bias the closure member 16 into position with regard to the seat member 12. The seat member includes a cutouts 43 in the flange members 28 which enables the sliding closure member 16 to be loaded into the seat 12 from a central position with a small sliding movement, in contrast to sliding the closure member along the entire length of the channel 22 from either direction.

The anchor 11 also includes a closure member 16 which acts with the seat 12 to present a closed anchor 11 which facilitates the manipulation and specifically, the derotation of the spine. Since the closure member has a dove-tailed relationship with the seat member 12 to allow a sliding interlocking engagement. The seat member 12 may be loaded from the top with the rod 20 and subsequently closed with the closure member 16 so as to fix the rod relative to the fixation means, but to allow rotation of the rod about its longitudinal axis. The closure member 16 includes projecting flanges 41 which have include a recess 39 on their upper surface, and a sliding shoulder 40 outward from the recess 39. The shoulders 40 of the closure member 16 form a dove-tailed cooperation with the shoulders 27 of the seat member, which cooperation inhibits the sliding closure member from being pulled out of the channel 22 of the seat member 12, and further which inhibits the sides 53, 54 of the seat member which form the channel 22 from splaying in response to a rotational force applied to the rod and cap member, respectively.

The closure member further includes a curved or arched rod interface surface 37 which mates with the top surface of the rod 20. The closure member 16 includes a hole 33 which is threaded with internal threads 34 to receive a set screw 18 having external threads 19. Thus, the set screw 18 can be screwed down relative to the closure member 16 to form a compressive interface with the rod 20. It is a further advantage that the set screw 18 includes a bevel 47 having serrations 48 and a countersink 49 to inhibit the stripping of the set screw and seat threads, as well as improve the compressive grip of the set screw on the rod 20.

In addition, the sliding member has opposing cutout sections 42 corresponding to the cutout section 43 of the seat member to facilitate an intermediate loading of the sliding closure member 16 relative to the seat 12. The seat member 12 has multiple grooves 30 which receive the protuberance 29 of the seat to cause a friction lock between the closure member and the seat member, which lock can be overcome by sliding the closure member along the longitudinal axis of the rod. The closure member has opposing retaining dimples on its front and rear surface which facilitate the assembly of the closure member relative to the seat using an instrument 78 shown in FIG. 8 of the present application. In addition, the set screw has a hex opening 46 to allow the set screw to be driven into engagement with the rod 20 using a hex driver.

An instrument 78 is shown for assembly of the closure member relative to the seat member and includes a handle 80 an 82 shaft of a length appropriate to allow the surgeon access to the implant, and a pronged instrument head 84. The head 84 includes an opening 86 of a size appropriate to receive the closure member 16, which opening 86 is defined first and second arms 85. The first and second arms respectively include a boss 88 and a spring loaded plunger ball 89. The ball is held in engagement relative to the closure member 16 by biasing means 90.

While in accordance with the Patent Statutes, the best mode and preferred embodiment has been set forth, the scope of the invention is not limited thereto, but rather by the scope of the attached claims.

What is claimed is:

1. A retaining member for use in retaining relative to the spine member an elongated member, the retaining member having a longitudinal axis and comprising:

a seat member having channel means extending along the longitudinal axis and having an opening in at least one side adapted to receive said elongated member and including a top opening defined by first and second lateral opposing surfaces which face inwardly with respect to said channel; attachment means adapted to attach the seat means to the spine member; and closure means having first and second spaced lateral surfaces which face away from each other and a longitudinal arch which cooperates with the channel means top opening for capturing the elongated member; the seat member having at least first and second seat member retaining flanges extending inwardly with respect to said channel means and along a direction parallel to said longitudinal axis, said first seat member retaining flange including said first lateral opposing surface and said second seat member retaining flange including said second lateral opposing surface, and the closure means including at least first and second closure means retaining flanges extending from the arch along a direction parallel to said longitudinal axis; and the seat member retaining flanges and the closure means flanges having a longitudinal sliding mating interface so as to close the top opening of the channel means along the longitudinal axis when the closure means is slid longitudinally into a closed position relative to the seat member; and said longitudinal sliding mating interface including means to create a longitudinal sliding interference fit between the closure means and the seat member so as to releasably retain the closure means by longitudinally sliding into said closure means to said closed position, the means to create the interference fit comprising at least one boss which forms a some portion of a cylinder on said first or second opposing lateral surface of the seat member or on said first or second spaced lateral surface of the closure means and a corresponding hollow on one of said lateral surfaces on the other of the closure means or the seat member respectively.

2. A retaining member as set forth in claim 1, wherein said means to create said longitudinal sliding interference fit comprises at least one boss on the closure means and a corresponding hollow on the seat member.

3. A retaining member as set forth in claim 2, wherein said boss has a smoothly curved surface in the direction of the longitudinal axis.

4. A retaining member as set forth in claim 3, wherein the cylinder portion of the at least one boss has a long axis perpendicular to the longitudinal axis.

5. A retaining member as set forth in claim 1, wherein said means to create said longitudinal sliding interference fit comprises at least one boss on the seat member and a corresponding hollow on the closure means.

6. A retaining member as set forth in claim 5, wherein said boss has a smoothly curved surface in the direction of the longitudinal axis.

7. A retaining member as set forth in claim 6, wherein the cylinder portion of the at least one boss has a long axis perpendicular to the longitudinal axis.

8. A retaining member as set forth in claim 1, wherein said seat member has a first end and a second end in the direction of the longitudinal axis and said first seat member retaining flange comprises two retaining flanges on one side of the channel means and said second seat member retaining flange comprises two retaining flanges on the other side of the channel means with first and second gaps between each set of seat member retaining flanges, and the first closure means retaining flange comprises two retaining flanges on one side of the longitudinal arch and the closure second means retaining flange comprises two retaining flanges on the other side of the arch with third and fourth gaps between each set of closure means retaining flanges, and the first and the second gaps are large enough for the closure means retaining flanges to pass through, and the third and the fourth gaps are large enough for the seat member retaining flanges to pass through so that the closure means can be mounted on the seat member from at least one end and from above and then slid into said closed position along the longitudinal axis.

9. A retaining member for use in retaining relative to the spine member an elongated member having a longitudinal axis, the retaining member comprising:

a seat member having channel means to receive said elongated member with a longitudinal axis between a first side and a second side and said channel means having at least an end opening and a top opening attachment means for attaching the seat means to the spine member and closure means which cooperate with the top opening of the channel means to capture the elongated member; the seat member having two retaining flanges on the first side of the channel means and two retaining flanges on the second side of the channel means with first and second gaps between each set of seat member retaining flanges, and the closure means has a central arch with a longitudinal axis between a first side and a second side with two retaining flanges on the first side and two retaining flanges on the second side of the arch with the third and fourth gaps between each set of closure means retaining flanges and the seat member retaining flanges and the closure means retaining flanges mating so as to close the top opening of the channel means along the longitudinal axis of the elongated member when the closure means is in a closed position relative to the seat member; and the first and the second gaps are large enough for the closure means flanges to pass through and the third and the fourth gaps are large enough for the seat member flanges to pass through so that the closure means can be mounted on the seat member from said end opening, and from above and slide into a closed position along the longitudinal axis of the elongated member.

10. A retaining member as set forth in claim 9, wherein the retaining means further comprises means to create an interference fit between the closure means and the seat member so as to releasably retain the closure means in said closed position in the longitudinal direction.

11. A retaining member as set forth in claim 9, wherein the attachment means comprises a hook.

12. A retaining member as set forth in claim 9, wherein the seat member is a symmetrical about a vertical plane perpendicular to the longitudinal axis.

13. A retaining member as set forth in claim 9, wherein the seat member flanges extend inward toward the direction of the longitudinal axis of the closure means flanges extend outward from the direction of the longitudinal axis, and the closure means cooperates internal to the seat member to close said channel means.

* * * * *